United States Patent
Boese et al.

(10) Patent No.: US 7,505,803 B2
(45) Date of Patent: Mar. 17, 2009

(54) SYSTEM OR METHOD FOR EXAMINING A PATIENT BY MEANS OF AN IMAGING MEDICAL DIAGNOSTIC EQUIPMENT

(75) Inventors: Jan Boese, Eckental (DE); Martin Kleen, Furth (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 108 days.

(21) Appl. No.: 11/340,209

(22) Filed: Jan. 26, 2006

(65) Prior Publication Data
US 2006/0173273 A1 Aug. 3, 2006

(30) Foreign Application Priority Data
Jan. 28, 2005 (DE) .................. 10 2005 004 142

(51) Int. Cl.
A47B 13/00 (2006.01)
A61B 5/05 (2006.01)

(52) U.S. Cl. .................. 600/407; 5/601; 600/425; 600/409; 600/436

(58) Field of Classification Search .......... 600/425, 600/407, 427; 5/601
See application file for complete search history.

(56) References Cited

U.S. PATENT DOCUMENTS

| | | | | |
|---|---|---|---|---|
| 4,926,866 A | * | 5/1990 | Lee | 600/301 |
| 5,097,495 A | * | 3/1992 | Gray et al. | 378/117 |
| 5,166,588 A | | 11/1992 | Goldhorn | |
| 5,805,664 A | | 9/1998 | Whipple, III et al. | |
| 5,916,160 A | * | 6/1999 | Arcan et al. | 600/407 |
| 6,023,166 A | * | 2/2000 | Eydelman | 324/318 |
| 6,026,318 A | * | 2/2000 | Bernstein et al. | 600/427 |
| 6,125,163 A | * | 9/2000 | Barth et al. | 378/4 |
| 6,280,392 B1 | | 8/2001 | Yoshimi et al. | |
| 6,450,957 B1 | | 9/2002 | Yoshimi et al. | |
| 6,661,240 B1 | * | 12/2003 | Johnson et al. | 324/662 |
| 6,719,708 B1 | | 4/2004 | Jansen | |
| 7,060,964 B1 | * | 6/2006 | Pi et al. | 250/227.14 |
| 2003/0128807 A1 | * | 7/2003 | Kotler et al. | 378/64 |
| 2003/0136201 A1 | | 7/2003 | Hubbard, Jr. | |
| 2005/0011738 A1 | * | 1/2005 | Smith et al. | 200/85 R |
| 2005/0124864 A1 | * | 6/2005 | Mack et al. | 600/300 |
| 2005/0251914 A1 | * | 11/2005 | Schaller et al. | 5/601 |
| 2006/0017437 A1 | * | 1/2006 | Vu | 324/309 |
| 2006/0152378 A1 | * | 7/2006 | Lokhorst et al. | 340/666 |
| 2007/0055140 A1 | * | 3/2007 | Kuroda | 600/423 |

FOREIGN PATENT DOCUMENTS

| | | |
|---|---|---|
| DE | 100 01 698 A1 | 4/2001 |
| GB | 2 389 911 A | 12/2003 |
| WO | WO 01/64103 A1 | 9/2001 |

* cited by examiner

*Primary Examiner*—Eric F Winakur
*Assistant Examiner*—Helene Bor

(57) ABSTRACT

In order to enable patient data to be reliably taken into account in a simple manner for examination by means of an imaging medical diagnostic equipment of a patient positionable on a table top of a patient table, it is provided according to the invention for an occupancy distribution exerted by the patient on the table top to be ascertained, patient data corresponding to this occupancy distribution, specifically in respect of body dimensions and/or body posture, to be determined, and the diagnostic equipment to be adjusted according to the patient data; to ascertain the occupancy distribution, there is advantageously provided a distribution of pressure sensors.

18 Claims, 3 Drawing Sheets

SYSTEM OR METHOD FOR EXAMINING A PATIENT BY MEANS OF AN IMAGING MEDICAL DIAGNOSTIC EQUIPMENT

CROSS REFERENCE TO RELATED APPLICATIONS

This application claims priority to the German application No. 10 2005 004 142.6, filed Jan. 28, 2005 and which is incorporated by reference herein in its entirety.

FIELD OF THE INVENTION

The invention relates to a system or method for the examination by means of an imaging medical diagnostic equipment of a patient positionable on a table top of a patient table.

BACKGROUND OF THE INVENTION

When using an imaging medical diagnostic equipment for examining a patient positionable on a table top of a patient table, patient data, in particular the patient's body posture on the table top and/or the patient's body dimensions are relevant both for carrying out the procedure and for subsequent evaluation. A number of examples of this relevance of patient data are given below.

The patient can be examined on the table top in various body postures, e.g. on his stomach or back or on his left or right side, the diagnostic equipment having to be adjusted on the one hand according to the relevant posture and, on the other, said posture having to be taken into account for subsequent evaluation. Not taking the body posture sufficiently into account can result in imprecise positioning of a particular area to be examined, so that any image produced during the examination in question cannot be used for diagnosis. In addition, for diagnosis of the image, paying inadequate attention to the body posture can result in an incorrect diagnosis, e.g. one relating to an incorrect part of the body.

In addition, the patient's particular body dimensions such as his weight distribution or his body shape are also relevant to the examination, since in the case of an x-ray examination, for example, the thickness and nature of a body part to be x-rayed must be taken into account for setting the radiation parameters. Insufficiently allowing for the body dimensions may result in an image that is low in contrast and possibly unusable for a diagnosis and, in the case of an x-ray examination, may increase the patient's radiation load.

SUMMARY OF THE INVENTION

The object of the invention is to enable patient data to be reliably taken into account in a simple manner when using an imaging medical diagnostic equipment to examine a patient positionable on a table top of a patient table.

This object is achieved by a system according to the claims and by a method according to the claims; advantageous embodiments are set forth in the associated dependent claims. A patient table and mat advantageous for the inventive determination of the occupancy distribution are also the subject matter of the claims.

Because of the automatically determinable occupancy distribution exerted by the patient on the table top, the at least position-specific patient data can be determined with low cost and complexity and a high degree of accuracy, and can be taken into account in a simple manner for the examination as a result of the diagnostic equipment being adjustable on the basis of said patient data. Fine adjustments made by the user can be avoided and an image produced during the examination can be improved in terms of its quality and diagnostic usability.

The occupancy distribution can be determined in a simple and reliable manner by a system component comprising binary-occupancy-value-detecting sensors distributed over the table top, particularly in the form of a two-dimensional sensor array, it being provided that each individual sensor at its relevant position on the table top detects the presence of a local occupancy by the patient as an occupancy value. The totality of all these local binary occupancy values forms the locally resolved occupancy distribution on the basis of which the patient data can be determined in respect of a body shape and a body posture by the second system component.

According to a low-cost and low-complexity embodiment of the invention, the sensors for detecting the binary occupancy values are provided in the form of optical sensors. Appropriately orienting the field of view of these optical sensors perpendicular to the table top allows the patient's outer contour and body posture on the patient table to be determined from the occupancy distribution ascertained using them. It is likewise possible to ascertain the occupancy distribution by means of inductive sensors detecting binary occupancy values.

For particularly simple and reliable determination of an occupancy distribution going beyond the occupancy distribution based solely on binary values in an information content, it is possible, according to one embodiment of the invention, to implement the first system component using continuous-occupancy-value-detecting sensors distributed over the table top, particularly in the form of a two-dimensional sensor array. From the occupancy distribution determined in this manner, it is possible to determine not only the patient's body shape and posture but also, for example, the patient's weight or volume distribution.

The distribution and number of the pressure sensors, e.g. according to embodiments of the invention, also in the form of piezo crystals or using liquid- or gas-filled pressure chambers, can be flexibly adapted to the required resolution accuracy of the occupancy distribution to be determined. With particularly low technical complexity, the pressure sensors can be accommodated in a mat that can be placed on the patient table; by means of such a mat, an existing patient table, for example, can be inexpensively refitted.

As part of the second system component there can be provided, in a particularly simple manner, a computer by means of which an EDP representation of the occupancy distribution is generated from which the patient data is then determined with database assistance.

The third system component is designed in particular to display the patient data, to communicate the patient data to the diagnostic equipment and/or for automatic adjustment of the diagnostic equipment on the basis of the patient data.

BRIEF DESCRIPTION OF THE DRAWINGS

The invention and further advantageous embodiments of the invention as set forth in features of the dependent claims will now be explained in greater detail with reference to exemplary embodiments schematically illustrated in the accompanying drawings, but without thereby limiting the invention to these exemplary embodiments, in which:

DETAILED DESCRIPTION OF THE INVENTION

Figure 1:
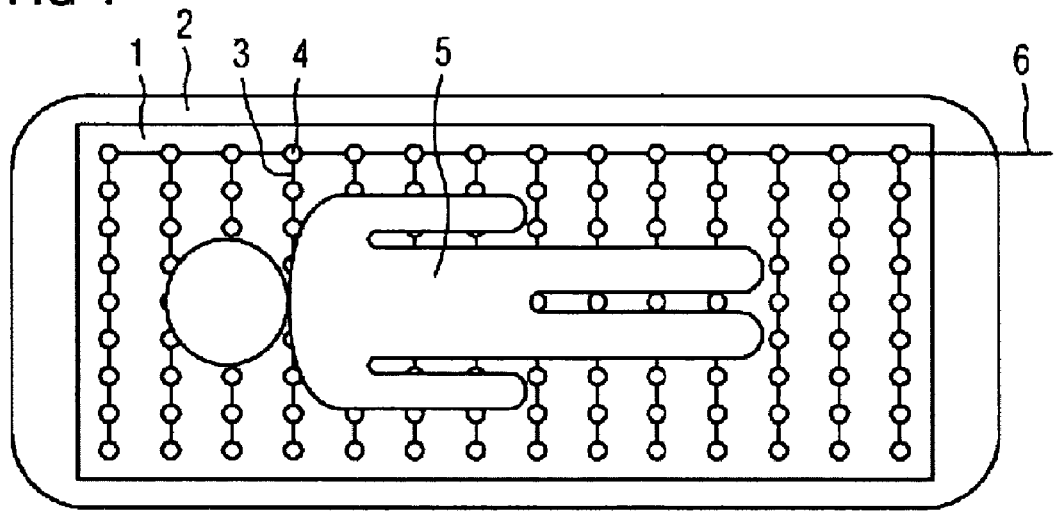
FIG. 1 shows a plan view of a patient table with a patient positioned on an interposed first system component in the form of a mat incorporating pressure sensors.

FIG. 1 shows a plan view of a patient table 2 with a first system component I disposed on the table top in the form of a mat 1 incorporating pressure sensors 4 and with a patient 5 positioned on said mat 1. The pressure sensors 4 interconnected by electric wires 3 form a sensor array with fourteen rows each comprising nine pressure sensors 4. Because of his weight distribution, the patient 5 exerts an occupancy distribution determined by these pressure sensors 4—explained below on the basis of pressure distribution—on the table top.

For particularly simple further processing of the pressure distribution, the pressures measured by the pressure sensors 4—as will be explained in greater detail below with reference to FIGS. 2 and 3—are converted into electrical output variables. These output variables are transmitted in an uncomplicated manner using an electrical communication link 6—as will be explained in greater detail below with reference to FIG. 4—from the first system component I to the second system component II.

Instead of the pressure sensors 4 being distributed in a mat 1 separately overlying the patient table 2 as shown in FIG. 1, one embodiment provides for the pressure sensors 4 to be disposed in the patient table 2 itself for particularly precise, secure fixing.

Figure 2:
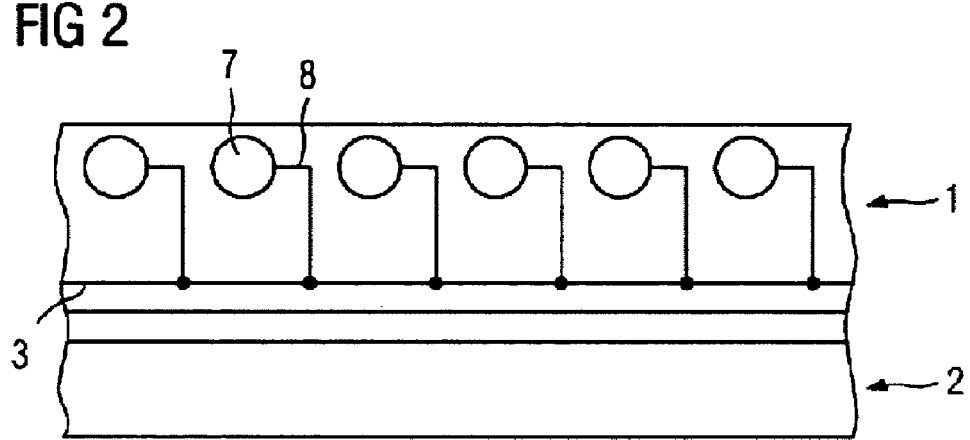
FIG. 2 shows a detail of a side-on view of the patient table according to FIG. 1 with pressure sensors in the form or piezo crystals.

FIG. 2 shows a detail of a side-on view of the patient table according to FIG. 1, the pressure sensors 4 being provided, according to one embodiment of invention, in the form of piezo crystals 7 which advantageously convert the pressure exerted on them directly into a pressure-dependent voltage convenient for simple transmission and further processing. The piezo crystals 7 are each connected via an electrical connection 8 to the electric wire 3.

Figure 3:
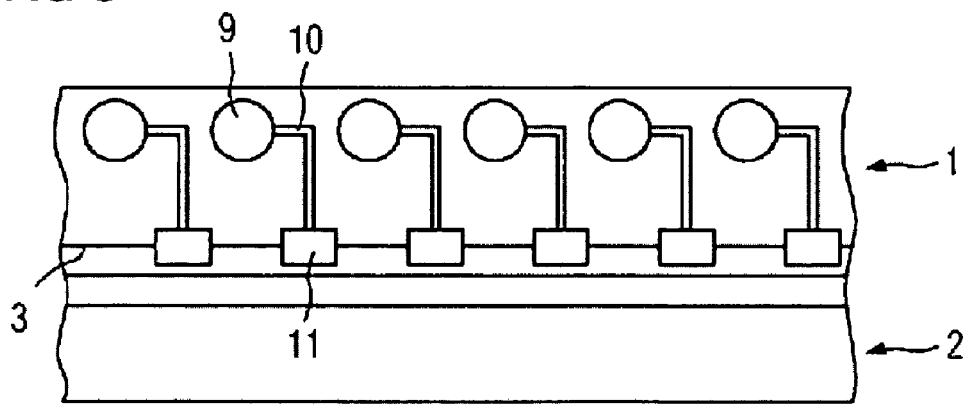
FIG. 3 shows a detail according to FIG. 2 with pressure sensors in the form of liquid-filled pressure chambers.

FIG. 3 shows a detail according to FIG. 2 in which the pressure sensors 4 are provided, according to one embodiment of the invention, in the form of liquid-filled pressure chambers 9 which can advantageously be flexibly adapted in their shape and size to the required structure of the sensor array in a simple and inexpensive manner. The internal pressure of these pressure chambers 9 depends on the external pressure exerted on them. Each pressure chamber 9 forwards its internal pressure via a pressure line 10 to a transducer 11 which converts the internal pressure into a voltage and passes it on to the electric wire 3. These transducers 11 need not, as illustrated, be disposed in the immediate vicinity of the pressure chambers, but can also be mounted remotely from them, e.g. on the edge of the mat 1.

According to an embodiment of the invention, it is alternatively provided for the relevant pressures to be determined in a particularly simple manner using pressure sensors in the form of conductors whose resistance varies with the pressure exerted on them. For a particularly compact design, there are provided, according to another embodiment of the invention, pressure sensors in the form of optical waveguides whose refractive index varies with the pressure exerted on them.

Figure 4:
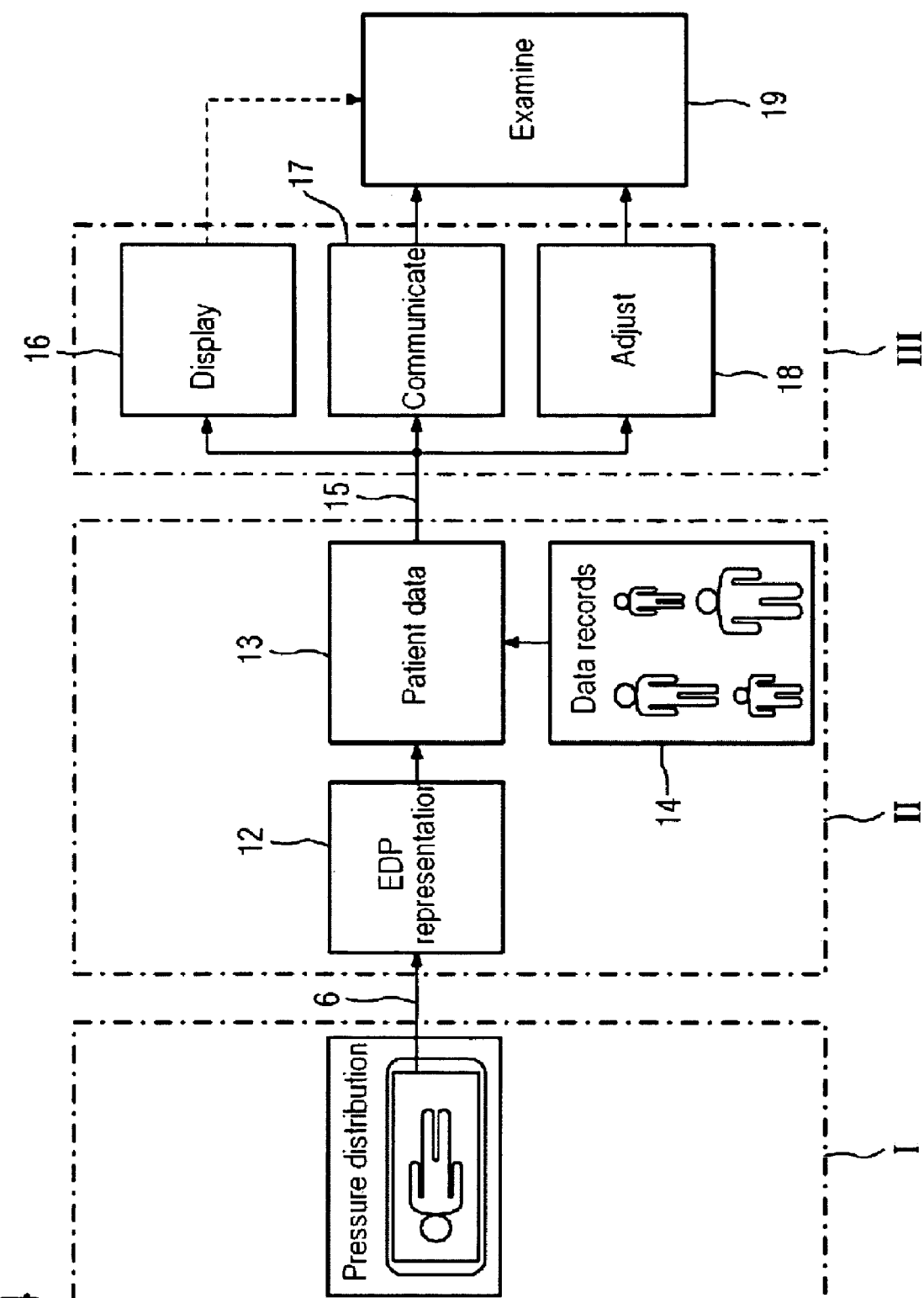
FIG. 4 shows the first, second and third system components and diagnostic equipment in their effective interrelationship.

FIG. 4 explains the effective interrelationship of the first system component I, the second system component II, the third system component III and a diagnostic equipment 19.

In the first system component I, the pressure distribution exerted on the table top of the patient table 2 by the patient 5 is determined using the pressure sensors 4 distributed in a mat 1.

This pressure distribution is forwarded via the communication link 6 to the second system component II which determines therefrom the patient data corresponding to the pressure distribution, in particular in respect of body dimensions and/or posture. For this purpose, according to one embodiment of the invention, an EDP representation is first generated from the pressure distribution e.g. using a data acquisition unit 12 as part of the second system component II, from which representation the patient data can be particularly easily determined by a computer 13 as part of the second system component II.

According to an advantageous embodiment, the body dimensions in respect of body weight distribution and/or body shape are determined from the EDP representation of the pressure distribution. In addition, it is advantageously provided for the body position in respect of body orientation on the table top and/or position of the body parts to be determined. For example, the body length can be derived from the greatest distance between two pressure sensors 4 on which a pressure is exerted, and the overall body weight from the sum of the individual pressures; the relevant body orientation can be obtained from a characteristic contour of the pressure distribution.

For particularly reliable determination of the patient data, according to another embodiment of the invention the assistance of a database 14 is provided which finds a correlation between the pressure distribution on the one hand and the possible body dimensions or postures on the other. This database 14 contains, in respect of body dimensions and posture, various data records as a reference pattern for the patient data, four of these data records being shown by way of example in FIG. 4. As in this exemplary embodiment, the relevant EDP representation of the pressure distribution can be compared by the computer 13 with the data records to determine the patient data. The database 14 can also contain an internal anatomy atlas which enables the patient data in respect of the position of internal organs of the patient 5 to be determined.

The patient data created in the second system unit II is forwarded via a data link 15 to the third system component III which is designed specifically to adjust the diagnostic equipment 19. Input errors occurring during user adjustment of the diagnostic equipment 19 can be prevented by the patient data being transmitted automatically thereto, e.g. by means of a data transfer device 17. Particularly advantageously for subsequent diagnosis on the basis of the image produced by the diagnostic equipment 19, it is provided for the patient data to be stored with this image, e.g. in its DICOM header. To ensure an examination particularly well matched to the patient 5, it is provided for the diagnostic equipment 19 to be adjusted automatically in respect of at least one image recording parameter, particularly relating to a particular examination area of the patient 5. This adjustment is performed in this exemplary embodiment by means of an adjusting device 18. For indirect adjustment of the diagnostic equipment 19 by the user or for user information, the patient data is displayed, specifically by means of a display device 16 provided for that purpose. On the basis of the body weight of the patient 5, if necessary the user can, for example, determine a required dose of a contrast agent or drug to be administered to the patient 5 for the examination, or this dose can be automatically determined by the system.

Figure 5:
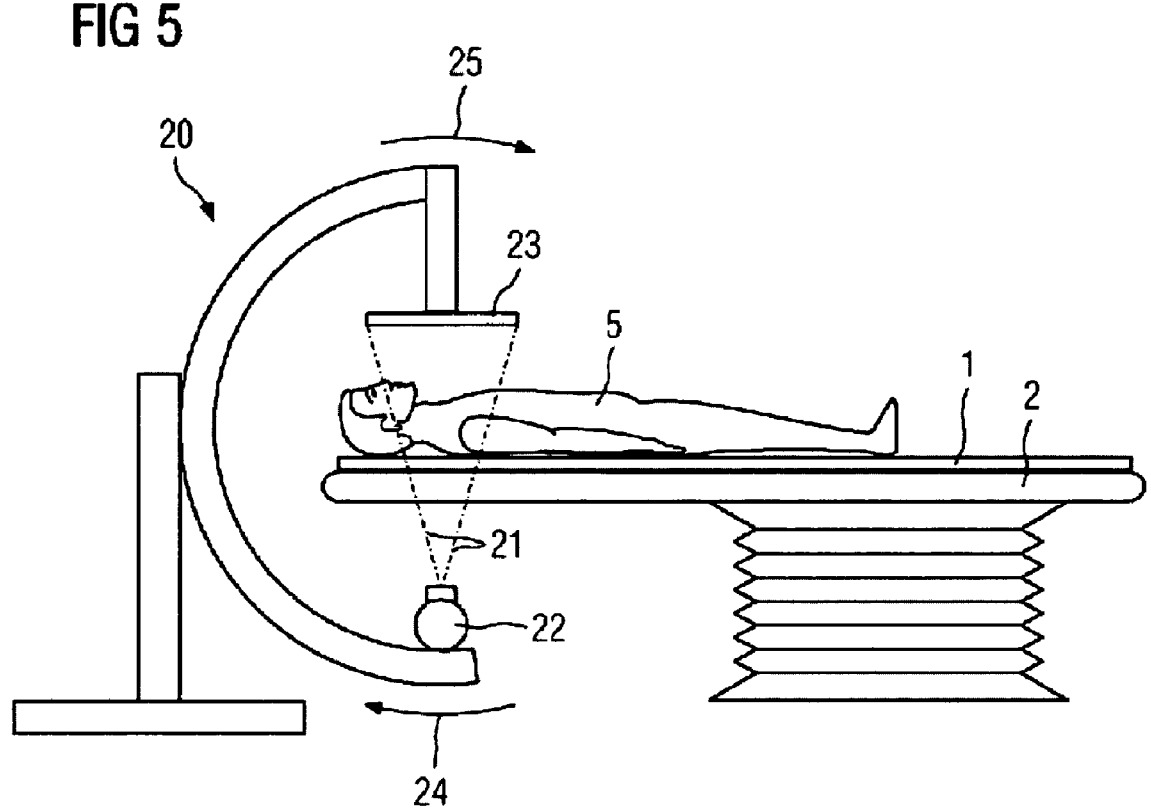
FIG. 5 shows a patient table according to FIG. 1 associated with a C-arm x-ray system.

As a practical example of the system according to the invention, FIG. 5 shows a patient table 2 according to FIG. 1 which is assigned to a C-arm x-ray machine 20. To advantageously reduce the radiation exposure of the patient 5 to the x-radiation 21 used for the examination, the C-arm x-ray equipment 20 is adjusted on the basis of the previously determined patient data in respect of the image recording parameters relating to a particular collimation area of the x-radiation 21 and/or corresponding to the radiation parameters.

For advantageous monitoring of the radiation load resulting from the intended examination, this is derived from the patient data so that a particular x-ray diagnostic equipment, in this exemplary embodiment the C-arm x-ray equipment 20, can be adapted in its setting to provide a required maximum radiation load. With recourse to the position of the internal organs, the radiation load of the particular organs exposed to the radiation can also be obtained.

In the case of rotational angiography, it is provided, according to an embodiment, for the C-arm x-ray equipment 20 to be adjusted, taking the patient data determined from the pressure distribution into account, in such a way that the isocenter of the C-arm x-ray equipment 20 is oriented to the relevant examination area of the patient 5, thereby enabling the examination area to be examined by x-radiation 21 in a particularly selective manner so that any unnecessary radiation load on the surrounding body tissue can be avoided.

For diagnostic equipment having at least one movable equipment part for performing the examination, it is provided, in order to advantageously avoid a collision with the patient 5, for the diagnostic equipment to be adjusted in respect of the image recording parameters relating to a particular movement sequence of the one or more equipment parts, taking the posture of the patient 5 determined from the pressure distribution into account, thereby making it possible e.g. in the case of rotational angiography using the C-arm x-ray system 20 to prevent in a particularly reliable manner the radiation emitter 22 and the radiation detector 23, which are rotated in directions 24 and 25 respectively for an examination, from colliding with the patient 5.

To avoid image defects such as movement blur and motion artifacts in an x-ray image or series of x-ray images or in a 3D image produced by means of rotational angiography, computer tomography, magnetic resonance, SPECT or PET, it is provided, according to an embodiment of the invention, for a movement behavior of the patient 5 determined from a time variation in the body posture to be taken into account. By displaying this movement behavior, the user can check before and during the examination whether the posture of the patient (5) is sufficiently still. Even for an intervention using a therapeutic equipment—e.g. for radiation therapy or shock wave therapy—it is advantageous for the time variation of the posture to be determined before and during the intervention in order to avoid treatment errors occurring because of a patient's body movement.

According to another embodiment of the invention for a magnetic resonance diagnostic equipment, the latter is adjusted in respect of the image recording parameters relating to a particular tuning of transmit coils and/or of receive coils on the basis of the patient data, thereby achieving improved image quality.

The adjustment of the collimation area and/or of the radiation parameters or the orientation to the patient 5 can be correspondingly transmitted to a computer tomography equipment, specifically in respect of the relevant field of view.

The invention may basically be summarized as follows: in order to enable patient data to be taken into account in a simple and reliable manner for the examination by means of an imaging medical diagnostic equipment of a patient positionable on a table top of a patient table, it is provided according to the invention for the occupancy distribution exerted by the patient on the table top to be determined; to ascertain the occupancy distribution, sensors, specifically in the form of pressure sensors, are incorporated directly in the patient table or sections of a mat placed on the patient table. Patient data corresponding to the occupancy distribution, particularly in respect of body dimensions and/or posture of the patient, is determined and the diagnostic equipment is adjusted according to this patient data.

The invention claimed is:

1. A system for the examination of a patient by an imaging medical diagnostic equipment that can be positioned on a table top of a patient table, comprising:
    a first system component for determining an occupancy distribution exerted by the patient on the table top, wherein the first system component is implemented using occupancy-value-detecting pressure sensors associated with the table top and distributed in the form of a two-dimensional sensor array;
    a second system component, linked to the first system component, for determining patient data corresponding to the occupancy distribution, in particular with respect to body dimensions and position of internal organs; and
    a third system component, linked to said second system component and to the diagnostic equipment, for directly adjusting the diagnostic equipment according to the patient data; wherein the diagnostic equipment comprises equipment for performing x-ray imaging, rotational angiography, computer tomography, magnetic resonance imaging, SPECT or PET; and wherein the third system component is implemented to automatically adjust the diagnostic equipment in respect of image recording parameters, specifically relating to a particular examination area of the patient.

2. The system according to claim 1, wherein the first system component is in the form of a two-dimensional optical sensor array.

3. The system according to claim 1, wherein a first system component is implemented using continuous-occupancy-value-detecting pressure sensors distributed in a mat over the table top and in the form of a two-dimensional sensor array.

4. The system according to claim 3, wherein the pressure sensors are distributed as components incorporated in the patient table.

5. The system according to claim 3, wherein the pressure sensors are implemented in the form of piezo crystals having output voltages that vary as a function of pressure.

6. The system according to claim 4, wherein the pressure sensors implemented in the form of liquid- or gas-filled pressure chambers have an internal pressure that varies as a function of pressure.

7. The system according to claim 4, wherein the pressure sensors implemented in the form of conductors have a resistance that varies as a function of pressure.

8. The system according to claim 4, wherein the pressure sensors implemented in the form of optical waveguides have a refractive index that varies as a function of pressure.

9. The system according to claim 4, wherein an electrical transmission link is provided from the first system component to the second system component by a pressure-dependent electrical output variable.

10. The system according to claim 1, wherein the diagnostic equipment is an x-ray system and is implemented for automatic adjustment of the image recording parameters relating to a particular collimation area and/or particular radiation parameters of the x-ray diagnostic equipment.

11. A method for the examination by imaging medical diagnostic equipment of a patient that is positioned on a table top of a patient table, comprising:
- automatically determining an occupancy distribution exerted by the patient on the table top by using binary-occupancy-value-detecting pressure sensors distributed over the table top and in the form of a two-dimensional sensor array;
- automatically determining patient data with respect to body dimensions and position of internal organs corresponding to the occupancy distribution; and
- adjusting the diagnostic equipment, directly, according to the patient data; wherein the diagnostic equipment comprises equipment for performing x-ray imaging, rotational angiography, computer tomography, magnetic resonance imaging, SPECT or PET, wherein adjusting comprises adjusting the diagnostic equipment in respect of image recording parameters, specifically relating to a particular examination area of the patient.

12. The method according to claim 11, wherein the body dimensions are determined by a body weight distribution and/or a body shape.

13. The method according to claim 11, wherein the body posture is determined by a body orientation on the table top and/or a position of body parts.

14. The method according to claim 11, wherein 3D rotational angiography is performed by a C-arm x-ray diagnostic equipment and the isocenter of the C-arm x-ray diagnostic equipment is oriented to the relevant examination area of the patient taking the patient data into account.

15. The method according to claim 11, wherein a magnetic resonance diagnostic equipment is adjusted with respect to the image recording parameters relating to a particular tuning of transmit coils and/or receive coils.

16. The method according to claim 11, wherein for adjustment of the diagnostic equipment the relevant movement state of the patient is determined from a time change in the posture is taken into account.

17. A system for examination of a patient comprising:
- a patient table for a patient positionable on the table top of the table; and
- an imaging medical diagnostic equipment;
- wherein the patient table comprises a plurality of pressure sensors for determining an occupancy distribution exerted by the patient on the table top and the plurality of pressure sensors are interconnected by wires to form a two-dimensional array, and
- wherein the diagnostic equipment comprises equipment for performing x-ray imaging, rotational angiography, computer tomography, magnetic resonance imaging, SPECT or PET that is linked to said plurality of pressure sensors and for adjusting image recording parameters responsive thereto.

18. The patient table as claimed in claim 17, further comprising a mat for placing on the table top for examination by imaging medical diagnostic equipment and incorporating a distribution of sensors for determining an occupancy distribution exerted by the patient on the table top.

* * * * *